United States Patent [19]

Paul et al.

[11] Patent Number: 4,788,466
[45] Date of Patent: Nov. 29, 1988

[54] PIEZOELECTRIC SENSOR Q-LOSS COMPENSATION

[75] Inventors: David W. Paul; Theodore L. Beeler, both of Fayetteville, Ark.

[73] Assignee: University of Arkansas, Little Rock, Ark.

[21] Appl. No.: 118,769

[22] Filed: Nov. 9, 1987

[51] Int. Cl.[4] .............................................. H01L 41/08
[52] U.S. Cl. ...................................... 310/316; 73/53; 73/32 A; 310/321; 310/323
[58] Field of Search ................ 310/316, 317, 321–324, 310/329, 338; 331/65; 73/32 R, 32 A, 54, 59, 53, 290 V, DIG. 4, 700, 384, 702, 703, 517 AV, 865, 865.5, 23, 24, 28, 29, 30; 177/210 R, 210 FP

[56] References Cited

U.S. PATENT DOCUMENTS

| | | | |
|---|---|---|---|
| 4,314,242 | 2/1982 | Kurv et al. | 310/321 X |
| 4,420,727 | 12/1983 | Rau | 310/316 X |
| 4,684,842 | 8/1987 | Maruno et al. | 310/316 |
| 4,687,962 | 8/1987 | Elbert | 310/316 |
| 4,721,874 | 1/1988 | Emmert | 310/316 X |

Primary Examiner—Mark O. Budd
Attorney, Agent, or Firm—Robert R. Keegan

[57] ABSTRACT

There is disclosed Q-loss compensation apparatus for a piezoelectric sensor such as a quartz crystal microbalance or other resonant vibratory device wherein the vibration amplitude of the device is controlled by negative feedback in a manner to obviate the effect of energy loss associated with viscous damping of a large liquid drop on the quartz crystal face serving as an environment for an experiment to measure mass deposited on the crystal face. The specific apparatus includes an oscillator circuit for the vibratory device in which two generally similar variable gain amplifiers provide the regenerative feedback for maintaining oscillation. The negative feedback amplitude control circuit serves to maintain constant the output from the variable gain amplifier following the quartz crystal in the oscillator loop, and it thus maintains at a near constant value the product of the crystal vibration amplitude and the square root of the total gain in the oscillator loop. This results in stable oscillation of the quartz crystal with little influence from changing conditions such as temperature, viscosity of the fluid, evaporation of the fluid, etc., at the same time producing a linear frequency change dependent on the quantity of mass deposited on the crystal face from the liquid environment. Frequency change is measured in a conventional manner with accuracy of about one part per ten million, thereby permitting determination of minute mass amounts on the order of one nanogram.

19 Claims, 2 Drawing Sheets

PIEZOELECTRIC SENSOR Q-LOSS COMPENSATION

The present invention relates to electronic control circuits for piezoelectric sensors such as quartz crystal microbalances, and more generally to resonant vibratory devices subject to viscous damping. More specifically the invention relates to piezoelectric quartz crystal vibratory mass measurement device and control circuit which is capable of highly accurate measurement of minute masses deposited chemically, or otherwise, on a face of the crystal from a liquid drop of substantial volume resting on the face of the crystal.

Piezoelectric quartz crystal microbalances have been known for well over a decade, but until recently their use has been limited to measurement of solids or aerosol droplets on a crystal face otherwise exposed to the atmosphere, or other gas phase environment. Such devices detect mass deposited on the crystal by frequency change and have been used for measuring thin film thickness in industrial processes, for pollution control apparatus, for gas chromotography, and other such purposes. See, for example, *Applications of Piezoelectric Quartz Crystal Microbalances* published by Elsevier Science Publishers B.V., Amsterdam, the Netherlands 1984 (ISBN 0-444-42277-3).

It would be highly desirable to have the capability of measuring solid mass deposited on or accreted to a surface of a quartz crystal from a liquid environment, but great dificulty has been encountered with such apparatus due to the viscous damping effect of the liquid environment which tends to make the quartz crystal vibration unstable, or suppress it altogether. Even moderate success with piezoelectric sensors for a liquid environment has generally been limited to very small liquid volumes on the order of a micro-liter. It is difficult to obtain reliable results in the study of chemical or bio-chemical processes where quantities are so minute.

Microbalance apparatus for a liquid environment was described in 1986 by Thompson et al. See M. Thompson, C. Arthur, and G. K. Dhaliwal, Analytical Chemistry, 58, 1206, 1986, "Liquid-Phase Piezoelectric and Acoustic Transmission Studies of Interfacial Immunochemistry". Thompson et al disclose a block diagram of a circuit which allows an AT cut piezoelectric to oscillate in liquids. Thompsons circuit is suitable for operation only in very small volumes of liquid. The apparatus of this invention has no such limitation concerning the volume of the liquid. See also T. Nomura and T. Nagamune, Analytica Chimica Acta, 142, 281, 1982, "Frequency Shifts of Piezoelectric Quartz Crystals Immersed in Organic Liquids". Their oscillator circuit is a single NPN transistor with the crystal grounded on one side and biased up to the base of the transistor on the other, similar to the standard Pierce-type oscillator (sold by International Crystal Manufacturing of Oklahoma City). It has been found to have serious limitations and deficiencies.

In accordance with the present invention apparatus including a control circuit and oscillator circuit for a piezoelectric crystal is provided which compensates for the viscous damping loss of a substantial volume of liquid in contact with the vibrating quartz crystal face in a stable manner. The viscous damping loss will also be referred to as the Q-loss by analogy to the Q or quality factor of resonant electronic circuits. A basic definition for quality factor (Q) is "2 pi times the ratio of the maximum stored energy to the energy dissipated per cycle at a given frequency".

The stable control provided by the electronic circuit and method of the present invention makes it possible to maintain stable oscillation of a piezoelectric sensor having a drop of liquid on a vibrating face with a volume up to 30 micro-liters or more. A drop of water from an eyedropper or pipette will typically have a volume of about 30 micro-liters and this is an adequate volume for observing many chemical or bio-chemical processes. Also it is possible to couple a larger volume of a syringe to an undetached drop from the syringe in a manner that does not increase the viscous damping, but permits diffusion of the solutes in the syringe to pass to and from the sensitive surface of the piezoelectric crystal.

According to the present invention electronic oscillator apparatus is provided to detect the electrical output from the vibrating crystal, amplify it, and return it in proper phase to drive the crystal and maintain the vibrations. In addition, electrical apparatus is provided to detect the amplitude of electrical signals in the oscillator circuit and provide a negative feedback loop to maintain such amplitude at a controlled level. What has been described thus far is generally conventional, but the apparatus of the present invention differs in that it is arranged with two variable gain amplifiers in the oscilator regenerative feedback loop. A first of the amplifiers amplifies the electrical signal taken from the piezoelectric crystal while the second amplifier receives and amplifies the output of the first amplifier, and supplies it to drive the crystal to maintain its vibration. Furthermore, the input signal for the negative feedback control loop is taken not from the piezoelectric crystal signal directly, but after it has been amplified by the first variable gain amplifier. It is therefore the amplitude of vibration of the crystal multiplied by the gain of one of the two amplifiers which is compared with a reference and maintained constant by the negative feedback control loop. The negative feedback control loop provides a signal which is used for gain control of each of the aforementioned variable gain amplifiers.

The empirical results of experimental testing have shown that this apparatus and the method it employs to control the oscillation of the piezoelectric crystal produces very stable measurement results in a microbalance mode (i.e. frequency change is linearly proportional to mass deposited on the crystal face). Reproducible results are obtained which are not extremely sensitive to temperature, atmospheric pressure, drop volume or viscosity, or other factors which one cannot maintain precisely constant as would be desired. The apparatus is sensitive to vibration, but known measures of a simple character can provide the vibration isolation adequate to prevent inaccuracy due to such a source.

A rigorous mathematic analysis of the control apparatus and method has not been made, and thus no substantiated theory is available to explain why the electronic circuit and method of the present invention provides much greater liquid volume tolerance, and superior stability, reliability, and reproducibility for measurement results as compared with conventional circuits and methods. These superior results are, however, substantiated by experimental use under actual operating conditions.

In addition to providing the features and advantages described above, it is an object of the present invention to provide a resonant vibratory mass measurement device including a regenerative feedback circuit for maintaining oscillation of the piezoelectric crystal and a negative feedback control circuit for maintaining the product of the crystal vibration amplitude with amplifier gain at a pre-determined reference level using variable gain amplifiers in the regenerative circuit.

It is another object of the present invention to provide such a device wherein the regenerative oscillator circuit includes two variable gain amplifiers, each provided with a gain control signal from a negative feedback control circuit.

It is still another object of the present invention to provide a piezoelectric crystal microbalance with an improved control circuit rendering it capable of accurate measurement of minute deposited mass in a liquid environment of substantial volume in contact with a vibrating face of the piezoelectric crystal.

It is a further object of the present invention to provide a piezoelectric crystal microbalance apparatus in which deposited mass density on the quartz crystal face produces a proportionate change in frequency, and wherein the amplitude of vibration of the quartz crystal is controlled through a negative feedback circuit in a manner which permits the microbalance to be reliably operative when the vibrating crystal face is exposed to a liquid drop of substantial volume.

Other objects and advantages will be apparent from a consideration of the following description in conjunction with the appended drawings, in which.

Figure 1:
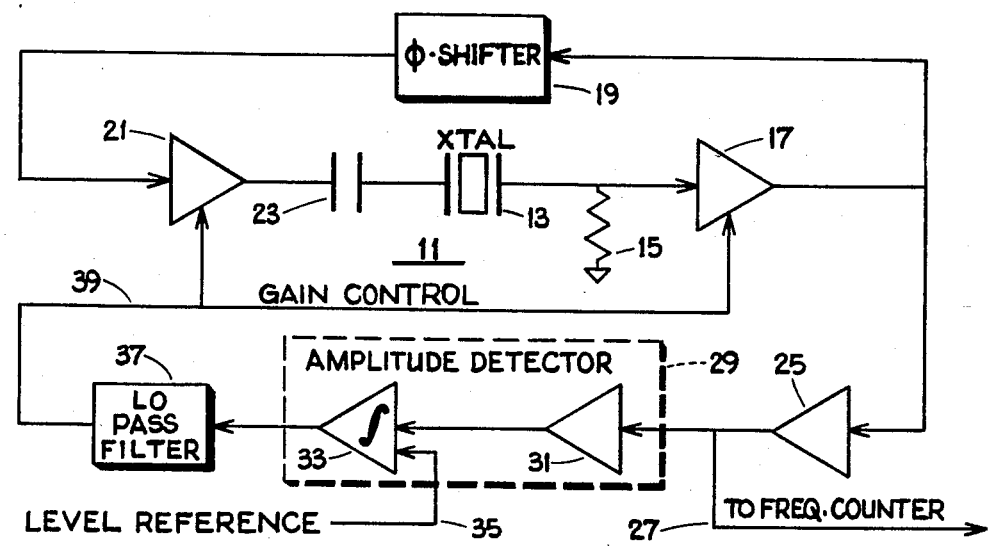
FIG. 1 is a schematic block diagram of an electronic control system according to the present invention.

Referring now to the drawings, and particularly to FIG. 1, a piezoelectric crystal microbalance electronic circuit having Q-loss compensation according to the invention is shown at 11. A piezoelectric sensor 13 preferably in the form of an AT cut quartz crystal is electrically connected in the circuit whereby the output from crystal 13 appears as a voltage across a resistor 15 and serves as the input to a variable gain amplifier 17. Typically the output of crystal 13 (and its mechanical vibration) will have a frequency of 10 megahertz approximately. The vibration is in a shear mode parallel to the crystal face. The output from the amplifier 17 is supplied to a phase shifter circuit 19 and from there to the input of another variable gain amplifier 21, which may be substantially identical to amplifier 17.

The signal output from amplifier 21 is fed through coupling capacitor 23 to drive crystal 13 at its resonant frequency of approximately 10 MHz. Each circuit element in the loop just described has an associated phase shift. Ideally, to sustain crystal vibration and therefore circuit oscillation, the net phase shift around the loop must be near zero or a multiple of 360° and the gain of the amplifiers must be at least sufficient to overcome losses in other circuit elements and in the crystal 13.

For example, if each amplifier, 21, 17 contributed 190° of phase shift and the combined phase shift of capacitor 23, crystal 13, and resistor 15 were 260° (equivalent to −100°) at resonance, then phase shifter 19 may have a phase shift of approximately 80°. The loop phase shifts thereby add to 720° with resulting in-phase or regenerative feedback through the loop.

The phase shift of the various elements in the loop described may be somewhat frequency sensitive, but the percentage variation in frequency in the circuit is not great so that differences in phase shift due to frequency change will not be substantial.

In addition to providing output to the feedback loop, the amplifier 17 output is provided to a substantially linear amplifier 25 which in turn provides the instrumentation output of the circuit to a frequency counter or other frequency measuring apparatus. As previously mentioned, changes in the frequency output of the circuit is measured with an accuracy of one part in ten million or better, whereby corresponding accretions on the crystal surface may be measured with an accuracy of nanograms.

The output of amplifier 25 also is transmitted to an amplitude detector 29, including an amplifier 31 and an integrating amplifier 33; an input 35 to amplifier 33 from a level reference such as a zener diode provides a constant reference level for the amplitude of the signal originally obtained from variable gain amplifier 17.

The function of the amplitude detector 29 is to provide a signal which is an amplified and integrated representation of the difference between the amplitude of the signal input to the amplitude detector 29 relative to a pre-determined reference established by the level reference input 35.

The output from amplitude detector 29 passes through a low pass filter 37 to provide a gain control input 39 to each of the amplifiers 17 and 21. Low pass filter 37 attenuates high frequency fluctuations which could adversely affect the gain control or possibly cause oscillation in the gain control feedback path. The combined time constant of the gain control feedback components including amplifier 25, amplitude detector 29 and low pass filter 37 is preferably about one millisecond. It will be noted that this time constant is vastly different from the period of the 10 megahertz oscillation of crystal 13 and the associated oscillator circuit.

The gain control portion of the circuit of FIG. 1 will be seen to act as a negative feedback servo-control for the vibration amplitude of crystal 13. In other words, decreasing amplitude of oscillation of crystal 13 causes an increase in the gain control signal provided to amplifiers 17 and 21, and consequently tends to drive up the amplitude of crystal 13 until the input to amplitude detector 29 is only very slightly less than the reference level set by input 35. That is to say, the gain control circuit operates to maintain the output from amplifier 17 substantially proportional to a constant level as determined by the input 35 from the level reference voltage.

The novel nature of the circuit can best be understood by considering conventional control techniques that might be applied to control the amplitude of oscillation of the crystal 13. If one wished to keep the amplitude of oscillation of the crystal at a constant value one could take an input for the amplifier 25 from the same source as the input to amplifier 17, such as the resistor 15. In such case the amplifier 25 would have no input from amplifier 17. Since the negative feedback loop including amplitude detector 29 and gain control output 39 operates to set the input of amplifier 25 to a constant level, the above described modification of the circuit would maintain the crystal amplitude constant. This would be a conventional approach and it has been found not to be very satisfactory for apparatus of the type described herein.

Another approach to amplitude control could take the output from amplifier 21 to supply the input to amplifier 25 rather than taking the amplifier 17 output as shown in FIG. 1. Following the previous analysis it will be seen that this would produce a device in which the driving signal for the crystal 13 was held constant, and this also would be a conventional approach which fails to provide the advantages of the present invention.

The operation of the circuit of FIG. 1 as shown will be seen to generate a signal at the output of amplifier 17 which is proportional to the amplitude of oscillation of the crystal 13 multiplied by the square root of the total gain for the oscillator circuit (provided by amplifiers 21 and 17). Explaining this further, it will be seen that if amplifier 17 has a momentary gain of 8 then amplifier 21 will also have a gain of 8 and the total gain for the oscillator circuit will be 64, i.e. 8 times 8. The output from amplifier 17 will be only 8 times the amplitude fo crystal 13, 8 being the square root of 64. It may be useful to take note of the fact that with the previously discussed modifications of FIG. 1 (to conform more nearly to the prior art) and again assuming a momentary gain of 8 for each of the amplifiers 21 and 17, an output from the input of amplifier 17 would have an amplitude of one times (i.e. equal to) the amplitude of the crystal 13, whereas a signal taken from the output of amplifier 21 would have an amplitude of 64 times the amplitude of the crystal 13.

In these discussions the fact that there are certain losses in the electronic components which have to be overcome by the gain of amplifiers 17 and 21 has been ignored. In fact a small part of the gain of amplifiers 17 and 21 serves to overcome constant losses in the electronic components, but this does not materially affect the above explanation of the operation of the circuit. If one wished to place a third (constant gain) amplifier in the oscillator regenerative feedback loop specifically to overcome losses due to electronic circuit components then it would be clear that the foregoing description of operation would be more precisely correct. As a practical matter such a separate amplifier is not necessary.

Figure 2:
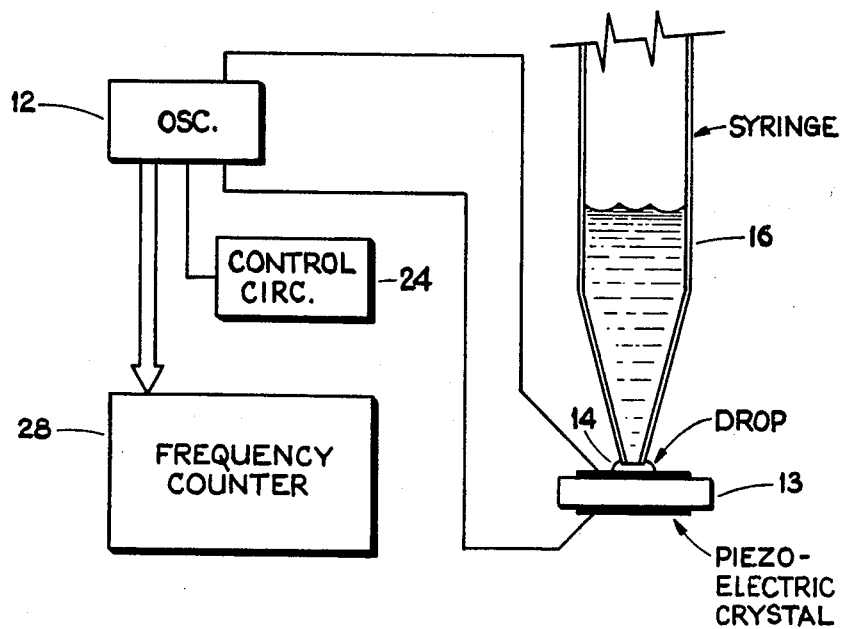
FIG. 2 is a schematic diagram of physical apparatus employing the electronic circuitry of the present invention.

The entire apparatus of which the control circuit of FIG. 1 is a part is shown in FIG. 2 in schematic form. The piezoelectric crystal 13 is appropriately mounted according to conventional piezoelectric crystal microbalance techniques and a drop of liquid 14, which is to be the liquid environment of the experiment, is deposited on the upper face of the crystal, which may be done by means of a syringe 16. In some cases the syringe 16 will be removed leaving a drop, with a volume of between 5 and 50 microliters for example, on the crystal 13. In other cases the syringe 16 may be maintained in the position shown in FIG. 2 where it will be noted that diffusion of the liquid or particles may take place between the drop and the syringe; however, liquid in the syringe is too remote from the crystal 13 to have significant viscous damping effect on the crystal. It should always be kept in mind that the vibration is preferably transverse and virtually no vibration takes place in a direction perpendicular to the face of the crystal.

Oscillator 12, of which the crystal 13 may be considered a part, maintains the oscillations of the crystal, and the control circuit 24 according to the invention controls the amplitude of oscillations of the crystal in a manner which permits accurate measurement of minute masses deposited on the crystal face from the liquid environment to a degree which has been impossible with previously known apparatus. Frequency counter 28 is utilized in a conventional manner to measure small frequency changes which are directly proportional to changes in mass deposited on the crystal face.

Although it has been empirically determined that the amplitude control circuit included in the apparatus of the present invention is very accurate and stable and that it has capabilities beyond that of any known prior circuits, there is no substantiated theory of exactly why these unexpected advantages accrue. Although some theoretical considerations will be discussed hereinafter it should be appreciated that the advantages and unobvious results accruing from incorporation of the control circuit of the invention in microbalance apparatus is not dependent upon theoretical analysis, but upon actual experimental results and empirical observations.

As mentioned previously the control circuit of FIG. 1 causes the output from amplifier 17 to be maintained at substantially a constant level and this output is an analog of the square root of the total gain times the crystal amplitude. In maintaining this value constant it may be observed that one also can consider the square of that function maintained constant. Therefore, the second power of the amplitude times the first power of the total gain is maintained constant. This means that if the total gain increases the square of the amplitude must decrease by a like factor and vice versa.

Considering the known general characteristics of friction forces and fluid or viscous damping, several observations can be made. Simple treatments of sliding friction where viscous damping is not involved consider that the frictional force is independent of the velocity. For very low velocities where fluid dynamics is involved, friction forces may be considered to be roughly proportional to velocity. However, it is safe to assume that low velocities are not predominant in the case of crystal microbalances vibrating at 10 MHz, and for such higher velocities fluid friction or viscous damping forces are generally considered to be proportional to the square of the velocity. In all cases there is a viscous drag coefficient determined by the physical dimensions and physical constants of the situation.

With frequency being relatively constant an increase in amplitude produces a proportionate increase in velocity, and thus viscous damping forces should be expected to be approximately proportional to the square of the amplitude of vibration of the crystal 13. On the other hand, mass and the effective viscous drag coefficient will enter into the force determination as linear or first power factors. From the foregoing explanation one might reasonably expect that changes in the square of the amplitude of crystal vibration could have a corresponding effect with changes in the first power of the gain, to the extent that gain is a measure of mass loading and/or effective viscous damping constant. The decrease of one would compensate increase of the other.

The foregoing suppositions are clearly not based on rigorous mathematical analysis, and are merely after the fact attempts to explain the reason for desirable operating characteristics which were achieved basically by experimental apparatus development.

It should be noted that the negative feedback signal of FIG. 1 for simplicity consists only of the signal which is an analog of amplitude times the square root of the gain. Possibly more complete Q-loss compensation could be achieved if allowance were made for one or more other higher or lower power terms in the expression for fluid friction force in addition to the second power term. As explained above the apparatus of FIG. 1 effectively holds the analog of the square of the amplitude times the gain to a constant level. Using operational amplifiers and conventional analog computer techniques one could replace the second power of the amplitude term with the sum of the first power times an appropriate constant plus the second power times an appropriate constant; this would, at least theoretically, more accurately represent the fluid dynamics of the viscous damping for the crystal microbalance. It should also be noted that the apparatus of FIG. 1 could be modified by adding one or more additional variable gain amplifiers in the feedback path, although there is no reason to believe that such an arrangement would be preferred in the usual case. With three variable gain amplifiers the output fed to amplifier 25 could be either the one-third power or the two-thirds power of the gain multiplied by the amplitude.

Also it has been assumed in the foregoing explanations that amplifiers 17 and 21 would be substantially identical and would be fed with identical gain control signals. That is not necessarily the case and one of the amplifiers 17 or 21 could be fed with a gain control signal greater than (for example, double) that of the other amplifier. Any other relationship between the gain control signals fed to the respective amplifiers could be prearranged. The preferred embodiment as presently known and understood is, however, to have the gain control signals to the gain control amplifiers 17 and 21 equal at any given moment.

Piezoelectric sensor or microbalance apparatus utilizing the invention has numerous new applications including monitoring electrochemical deposition, DNA Hybridization, corrosion studies, bio-chemical studies concerning enzyme analysis or water quality, or any situation where molecules are attracted to or leave from a surface surrounded by a liquid.

Figure 3:
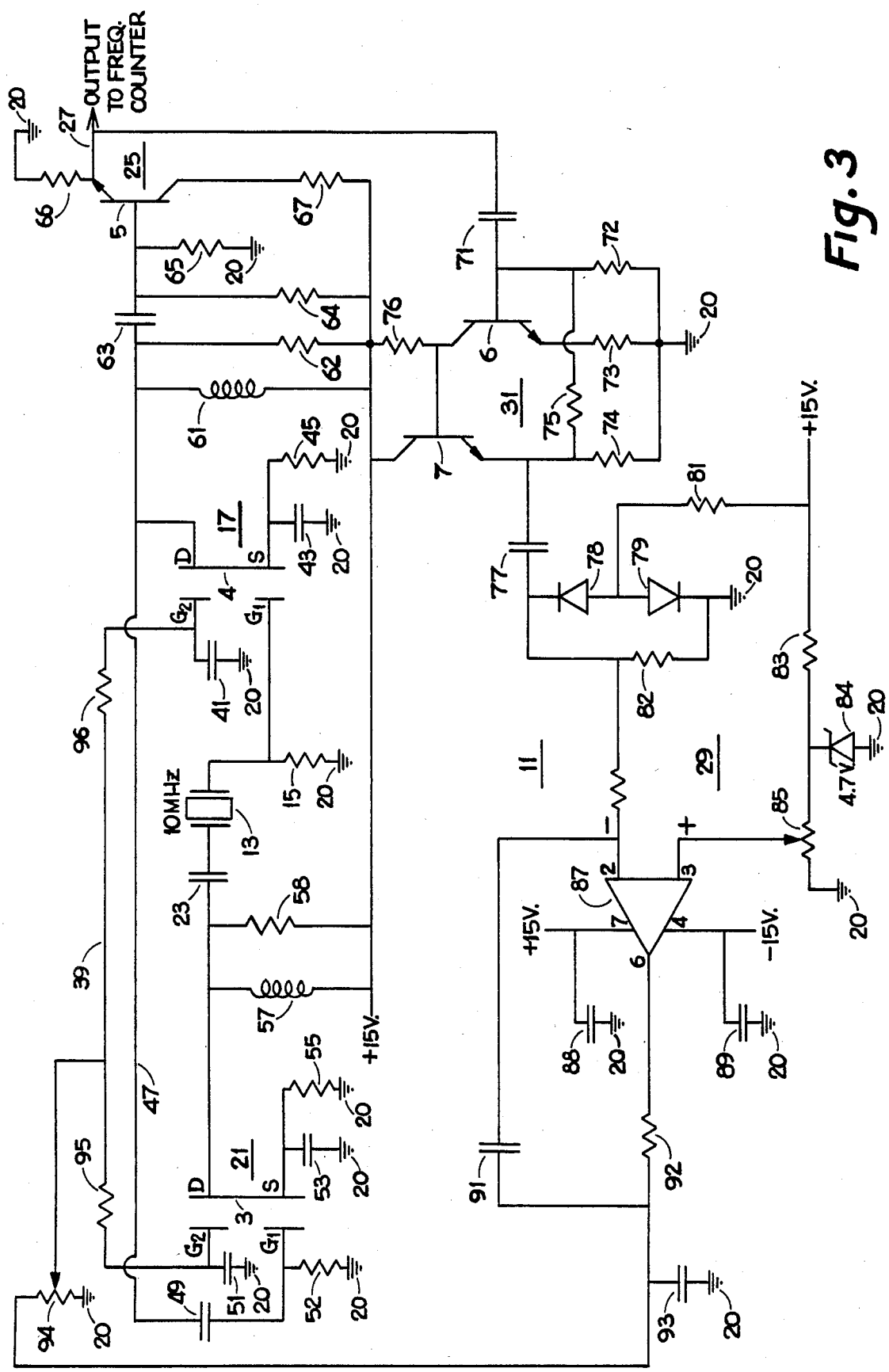
FIG. 3 is a detailed circuit diagram of an electronic circuit according to the present invention.

While the system illustrated in FIG. 1 can be implemented in various ways with conventional electronic circuitry a specific embodiment is shown in FIG. 3. Crystal 13 produces a substantially sinusoidal output at approximately 10 MHz which appears as a voltage across resistor 15 connected to ground 20. This voltage signal is coupled to a high input impedance amplifier 17 which may be a dual gate MOSFET amplifier connected to act as a variable gain amplifier. This amplifier and the corresponding amplifier 21 are preferably linear as respects the amplifier signal, but may be either linear or non-linear in respect to the response to the gain control input signal.

Amplifier 17 includes field effect transistor 4 and associated circuit elements including capacitor 41, capacitor 43, and resistor 45 all connected to ground 20. Amplifier 17 provides a relatively low output impedance and produces an output which appears as a voltage across inductor 61 and resistor 62 and across coupling capacitor 49, and resistor 52 in the input circuit of companion amplifier 21. Conductor 47 provides the feedback path from amplifier 17 to amplifier 21. As previously mentioned amplifier 21 may conveniently be a duplicate of amplifier 17; it includes field effect transistor 3 together associated circuit components capacitor 51, resistor 52, capacitor 53, and resistor 55. Amplifier 21 has a relatively low impedance output which appears as voltage across inductor 57 in parallel with resistor 58. This voltage is coupled through capacitor 23 to drive crystal 13 with a regenerative feedback signal which is properly phased by the phase shifts of the inductor and capacitor elements in the feedback loop. In the schematic diagram of FIG. 1 the phase shifts have been illustrated as lumped in one phase shifter element, but all contributions to the loop phase shift are in fact represented thereby.

The output from amplifier 17 is coupled through capacitor 63 to the base of transistor 5 serving as input of amplifier 25 which includes transistor 5 together with associated circuit components including resistor 64, resistor 65, resistor 66, and resistor 67.

The output from the emitter of transistor 5 and amplifier 25 is provided to the frequency counter of conventional form which serves as the instrumentation output for the circuit.

The output from the emitter of transistor 5 is also provided to the input of amplifier 31 through capacitor 71. Amplifier 31 includes transistor 6, transistor 7, and the associated resistors 72, 73, and 74 connected to ground 20, and resistors, 75 and 76.

The output from the emitter of transistor 7 is coupled through capacitor 77 to a bridge consisting of back-to-back diodes 78 and 79 together with resistor 82 and resistor 81. These components and the bridge they form serve to set a stable DC level for the AC output from amplifier 31, and they form a part of the amplitude detector 29. The output from amplifier 31 is fed through resistor 86 to one of the inputs of difference amplifier 87, designated as the negative input. The other (positive) input of amplifier 87 is provided with a constant DC voltage level reference from potentiometer 85 connected in series with resistor 83 between the positive (15 volt) voltage supply and ground 20. A zener diode 84 is connected in parallel with potentiometer 85 so that the full voltage across potentiometer 85 is equal to the zener diode reference voltage (for example, 4.7 volts). Amplifier 87 together with its associated components capacitor 88 and 89, is supplied with voltage from positive and negative voltage supplies. Amplifier 87 provides an output corresponding to the integrated difference of the signal originating from amplifier 17 relative to a voltage level reference established by the circuit associated with zener diode 84.

The values for capacitor 91 and resistor 86 are selected to provide a relatively long time constant for the output of amplifier 87; this time constant may be on the order of one millisecond. Values and type designations for circuit elements are shown in Table I below.

The output from amplifier 87 is further smoothed or filtered by capacitor 93 connected to ground 20 in parallel with the resistance of potentiometer 94. The center tap of potentiometer 94 is connected to the gain control lead 39 which supplies gain control signals through resistors 95 and 96 respectively to field effect transistors 3 and 4.

The operation of the specific circuit shown schematically in FIG. 3 is as previously described with reference to the schematic block diagram of FIG. 1 and will not be repeated in detail here. The particular circuit shown in FIG. 3 is only one of many electronic circuit combinations which could be utilized to implement the control system generally shown in FIG. 1. The circuit illustrated employs analog computation, but digital circuits could be substituted in whole or in part for the control functions.

TABLE I

| RESISTORS | |
|---|---|
| REFERENCE NOS. | OHMS |
| 15, 52 | 470 |
| 45, 55 | 100 |
| 62, 58 | 1.2K |

TABLE I-continued

| | |
|---|---|
| 64, 86, 95, 96 | 10K |
| 65 | 4.7K |
| 66 | 560 |
| 67 | 15 |
| 72 | 2.2K |
| 73 | 330 |
| 74 | 820 |
| 75 | 3.3K |
| 76, 82, 85, 92 | 2K |
| 81, 83 | 1K |
| 94 | 20K |

CAPACITORS

| REFERENCE NOS. | MICROFARADS |
|---|---|
| 23, 49 | .00001 |
| 41, 63, 51 | .001 |
| 43, 53, 71 | .01 |
| 77, 88, 89, 91, 93 | 0.1 |

INDUCTORS

| REFERENCE NOS. | MICROHENRYS |
|---|---|
| 57, 61 | 220 |

SEMICONDUCTORS

| REFERENCE NOS. | TYPE NO. |
|---|---|
| 3, 4 | 3N211 |
| 5, 6, 7 | 2N3904 |
| 78, 79 | 1N4148 |
| 87 | 741 |
| 84 | IN5320B(4.7v) |

In addition to the variation or modifications to the apparatus of the invention described or suggested above, other variations will be apparent to those of skill in the art, and accordingly the scope of the invention is not to be considered to be limited to the particular embodiments shown or suggested, but is rather to be determined by reference to the appended claims.

What is claimed is:

1. A resonant vibratory mass measurement device comprising
   (A) an electrically vibratable naturally resonant structure with a surface substantially parallel to the principle direction of vibration of said structure, said surface being adapted to receive a drop of liquid exceeding one micro-liter, and
   (B) means for causing vibration of said structure at above audible frequencies including
      (a) electrodes on said structure for supplying electrical signals to and from said structure,
      (b) means for generating a signal responsive to the frequency and amplitude of vibration of said structure,
      (c) a first variable gain amplifier connected to receive a signal from the means of (b),
      (d) a second variable gain amplifier connected to receive a signal from said first variable gain amplifier, and further connected in a feedback path to supply a signal to cause vibration of said resonant structure,
      (e) means for generating a reference signal,
      (f) comparison means connected to receive a signal responsive to said first variable gain amplifier to be compared with said reference signal and adapted to produce a control signal responsive to the amplitude difference therebetween, and
      (g) means for supplying said control signal to the respective gain control inputs of said first variable gain amplifier and said second variable gain amplifier.

2. Apparatus as recited in claim 1 further including a frequency counter connected to receive a signal from the means of (b).

3. Apparatus as recited in claim 1 wherein said resonant structure is a piezoelectric device.

4. Apparatus as recited in claim 3 wherein said device is an AT cut quartz crystal with a resonant frequency above 1 MHz.

5. Apparatus as recited in claim 3 wherein said device is a crystal vibratable in a shear mode.

6. Apparatus as recited in claim 3 wherein the amplifiers of (c) and (d) have similar characteristics and are supplied with the same gain control signal.

7. A resonant vibratory mass measurement device comprising
   (A) an electrically vibratable resonant structure with a surface substantially parallel to a direction of vibration of said structure, said surface being adapted to receive a volume of liquid in contact therewith, and
   (B) means for causing vibration of said structure near its resonant frequency including
      (a) means for supplying electrical signals to and from said structure,
      (b) means for generating a signal responsive to amplitude of vibration connected to said structure,
      (c) a first variable gain amplifier connected to receive a signal from the means of (b),
      (d) a second variable gain amplifier connected to receive a signal from said first variable gain amplifier, and further connected to supply a signal to cause vibration of said resonant structure,
      (e) means connected to receive a signal, at least in part, from said first variable gain amplifier to be compared with a reference signal and adapted to produce a control signal responsive to the difference therebetween, and
      (f) means for supplying said control signal to the respective gain control inputs of said first variable gain amplifier and said second variable gain amplifier.

8. Apparatus as recited in claim 7 further including a frequency counter connected to receive a signal from the means of (a).

9. Apparatus as recited in claim 7 wherein said resonant structure is a piezoelectric device.

10. Apparatus as recited in claim 9 wherein said device is an AT cut quartz crystal with a resonant frequency above 1 MHz.

11. Apparatus as recited in claim 9 wherein said device is a crystal vibratable in a shear mode.

12. Apparatus as recited in claim 9 wherein the amplifiers of (c) and (d) have similar characteristics and are supplied with the same gain control signal.

13. The method of controlling the amplitude of a resonant vibratory device subject to viscous damping comprising the steps of
   (a) detecting the amplitude and frequency of vibration of said device, and producing a signal representative thereof,
   (b) amplifying the signal of (a) with a gain which is controllable by a gain control signal,
   (c) amplifying the output from step (b) with a gain which is controllable by a gain control signal,
   (d) supplying the output from step (c) to said device with the proper phase to sustain vibration of said device, (e) generating a signal with a parameter that is a function of the amplitude of the output from step (b), comparing it with a known reference, and using the difference therebetween to produce a gain control signal which controls the gains of step (b) and (c).

14. The method as recited in claim 13 further including measuring the frequency of the signal from step (a).

15. The method as recited in claim 13 wherein said device is an AT cut quartz crystal with a resonant frequency above 1 MHz.

16. The method as recited in claim 13 wherein the amplifications of (b) and (c) have the same gain control.

17. The method of controlling the amplitude of a resonant vibratory device subject to viscous damping comprising the steps of
    (a) detecting vibration of said device, and producing a signal representative thereof,
    (b) amplifying the signal of (a) with a gain which is controllable by a gain control signal,
    (c) supplying output from step (b) to said device with the proper phase to sustain vibration of said device,
    (d) generating a signal with a parameter that is a function of the Nth power of the amplitude of vibration of said device and the Mth power of the total gain of step (b) where N is greater than M, and
    (e) supplying a gain control signal for step (b) to cause the signal parameter of step (d) to be maintained approximately at a constant level.

18. The method as recited in claim 17 further including the step of measuring the frequency of the signal from step (a).

19. The method as recited in claim 17 wherein the parameter of step (d) is a function of the Nth power of the amplitude of vibration of said device times the Mth power of the total gain of step (b).

* * * * *